US011186790B2

(12) United States Patent
Goossen et al.

(10) Patent No.: US 11,186,790 B2
(45) Date of Patent: Nov. 30, 2021

(54) BIOFUEL AND METHOD FOR PREPARATION BY ISOMERIZING METATHESIS

(71) Applicant: Umicore AG & Co. KG, Hanau-Wolfgang (DE)

(72) Inventors: Lukas Goossen, Bochum (DE); Kai F. Pfister, Kaiserslautern (DE); Sabrina Baader, Kaiserslautern (DE)

(73) Assignee: Umicore AG & Co. KG

( * ) Notice: Subject to any disclaimer, the term of this patent is extended or adjusted under 35 U.S.C. 154(b) by 212 days.

(21) Appl. No.: 16/084,786

(22) PCT Filed: Mar. 15, 2017

(86) PCT No.: PCT/EP2017/056176
§ 371 (c)(1),
(2) Date: Sep. 13, 2018

(87) PCT Pub. No.: WO2017/158060
PCT Pub. Date: Sep. 21, 2017

(65) Prior Publication Data
US 2019/0071611 A1 Mar. 7, 2019

(30) Foreign Application Priority Data
Mar. 15, 2016 (EP) ..................... 16160396

(51) Int. Cl.
*C07C 67/333* (2006.01)
*C10L 1/02* (2006.01)
(Continued)

(52) U.S. Cl.
CPC ............. *C10L 1/026* (2013.01); *B01J 31/00* (2013.01); *B01J 31/2217* (2013.01);
(Continued)

(58) Field of Classification Search
CPC ............. C10L 1/026; C10L 2200/0476; C10L 2270/026; B01J 31/2295; B01J 2231/49;
(Continued)

(56) References Cited

U.S. PATENT DOCUMENTS

2011/0306815 A1* 12/2011 Hagadorn ........... C07F 15/0046
585/638
2013/0204022 A1* 8/2013 Snead .................. C10G 29/205
554/125

OTHER PUBLICATIONS

Dominik M. Ohlmann, Nicole Tschauder, Jean-Pierre Stockis, Käthe Gooßen, Markus Dierker, and Lukas J. Gooßen, Isomerizing Olefin Metathesis as a Strategy to Access Defined Distributions of Unsaturated Compounds from Fatty Acids, Journal of the American Chemical Society, 134(33) 13716-13729 (Year: 2012).*

(Continued)

*Primary Examiner* — Ellen M McAvoy
*Assistant Examiner* — Ming Cheung Po
(74) *Attorney, Agent, or Firm* — Faegre Drinker Biddle & Reath LLP (57) ABSTRACT

Subject of the invention is a process for producing a biofuel from fatty acid methyl esters (FAMEs) obtained by transesterification of vegetable oils, comprising the steps of: (a) ethenolysis of the fatty acid methyl esters in the presence of ethylene and an ethenolysis catalyst, and (b) isomerizing metathesis in the presence of an isomerization catalyst and a metathesis catalyst. The invention also relates to biofuels obtainable by the inventive process and to uses of ethylene for adjusting and optimizing biofuels.

19 Claims, 2 Drawing Sheets

(51) Int. Cl.
*B01J 31/22* (2006.01)
*C07C 6/04* (2006.01)
*C07C 67/475* (2006.01)
*C10G 3/00* (2006.01)
*B01J 31/00* (2006.01)
*B01J 31/24* (2006.01)

(52) U.S. Cl.
CPC ....... *B01J 31/2291* (2013.01); *B01J 31/2295* (2013.01); *B01J 31/24* (2013.01); *C07C 6/04* (2013.01); *C07C 67/333* (2013.01); *C07C 67/475* (2013.01); *C10G 3/42* (2013.01); *B01J 2231/49* (2013.01); *B01J 2231/52* (2013.01); *B01J 2231/543* (2013.01); *B01J 2531/821* (2013.01); *B01J 2531/824* (2013.01); *C07C 2523/46* (2013.01); *C07C 2531/22* (2013.01); *C10L 2200/0476* (2013.01); *C10L 2270/026* (2013.01); *C10L 2290/542* (2013.01); *C10L 2290/543* (2013.01); *C10L 2290/544* (2013.01); *C10L 2290/547* (2013.01); *Y02E 50/10* (2013.01); *Y02P 30/20* (2015.11)

(58) Field of Classification Search
CPC .............. B01J 2231/52; B01J 2231/543; B01J 2531/821; B01J 2531/824; C07C 6/04; Y02P 30/20
See application file for complete search history.

(56) References Cited

OTHER PUBLICATIONS

Dominik M. Ohlmann, Nicole Tschauder, Jean-Pierre Stockis, Käthe Gooßen, Markus Dierker, Lukas J. Gooßen, Isomerizing Olefin Metathesis as a Strategy To Access Defined Distributions of Unsaturated Compounds from Fatty Acids, Jul. 20, 2012, J. Am. Chem. Soc, 134, 33, 13716-13729 (Year: 2012).*

Dominik M. Ohlmann, Nicole Tschauder, Jean-Pierre Stockis, Käthe Gooßen, Markus Dierker, and Lukas J. Gooßen, Isomerizing Olefin Metathesis as a Strategy To Access Defined Distributions of Unsaturated Compounds from Fatty Acids, 2012, American Chemical Society, p. 13718-13729 (Year: 2012).*

Dominik M. Ohlmann, Nicole Tschauder, Jean-Pierre Stockis, Kathe Goolien, Markus Dierker, and Lukas J. GooBen, Isomerizing Olefin Metathesis as a Strategy To Access Defined Distributions of Unsaturated Compounds from Fatty Acids, 2012, American Chemical Society, p. 13718-13729 (Year: 2012).*

Renee M. Thomas, Benjamin K. Keitz, Timothy M. Champagne, and Robert H. Grubbs, Highly Selective Ruthenium Metathesis Catalysts for Ethenolysis, 2011, American Chemical Society, pp. 7490-7496 (Year: 2011).*

Anderson, D., et al., "Synthesis and Reactivity of Olefin Metathesis Catalysts Bearing Cyclic (Alkl)(Amino) Carbenes", Angew. Chem. Int. Ed., 2007, vol. 46, pp. 7262-7265.

Baader, S., et al., "Synthesis of tsetse fly attractants from a cashew nut shell extract by isomerising metathesis", Green Chemistry, 2014, vol. 16, pp. 4885-4890.

Lavallo, V., et al., "Stable Cyclic (Alkyl)(Amino) Carbenes as Rigid or Flexible, Bulky, Electron-Rich Ligands for Transition-Metal Catalysts: A Quaternary Carbon Atom Makes the Difference", Angew. Chem. Int. Ed., 2005, vol. 44, pp. 5705-5709.

Marx, V., et al., "Cyclic Alkyl Amino Carbene (CAAC) Ruthenium Complexes as Remarkably Active Catalysts for Ethenolysis", Angew. Chem. Int. Ed., 2015, vol. 54, pp. 1919-1923.

Montenegro, R., et al., "Lowering the boiling point curve of biodiesel by cross-methathesis", Eur. J. Lipid Sci. Technol., 2012, vol. 114, pp. 55-62.

Ohlmann, D., et al., "Isomerizing Olefin Metathesis as a Strategy To Access Defined Distributions of Unsaturated Compounds from Fatty Acids", Journal Of The American Chemical Society, 2012, vol. 134, p. 13716-13729.

Pfister, K., et al., "Isomerizing Metathesis as an Efficient Tool for the Generation of Biodiesel from Rapeseed Oil", 8th Workshop on Fats and Oils as Renewable Feedstock for the Chemical Industry, 2015, p. 1.

International Preliminary Report on Patentability for PCT/EP2017/056176 dated May 22, 2017.

International Search Report for PCT/EP2017/056176 dated May 22, 2017.

Written Opinion of the International Searching Authority for PCT/EP2017/056176 dated May 22, 2017.

* cited by examiner

BIOFUEL AND METHOD FOR PREPARATION BY ISOMERIZING METATHESIS

CROSS-REFERENCE TO RELATED APPLICATIONS

This application is a national stage application (under 35 U.S.C. § 371) of PCT/EP2017/056176, filed Mar. 15, 2017, which claims benefit of European Application No. 16160396.4, filed Mar. 15, 2016, both of which are incorporated herein by reference in their entirety.

The invention relates to a process for producing biofuel from fatty acid methyl esters (FAMEs) obtained by transesterification of vegetable oils. The invention also relates to biofuels obtained by the inventive process and to uses of ethylene for adjusting and optimizing biofuels.

STATE OF THE ART

The increasing environmental awareness and upcoming shortage of fossil oil-derived fuels have triggered a growing demand for biofuels derived from plant oils. Biodiesel is presently generated by transesterification of vegetable oils or animal fats with methanol, which transforms the triacylglycerols to fatty acid methyl esters (FAMEs) and glycerol. Around 80% (107 Mt/a) of the worldwide plant oil production is required to cover food demands, the remaining 20% are converted into biofuels (11 Mt/a) or put to other industrial uses (15 Mt/a). In the European Union, a FAME content of 7% in diesel fuel is currently imposed by EN 590, and an increase to 10% is planned by 2020.

Besides being a renewable and biodegradable material of domestic origin, biodiesel has some beneficial properties over conventional diesel, such as its inherent lubricity, lower sulphur content, and higher flash point. When added in small quantities, FAMEs have mostly advantageous effects on the properties of diesel fuel. However, the use of biodiesel in larger percentages or in pure form is problematic due to its instability towards oxidation, high viscosity and pour point, as well as an increased release of nitrogen oxides. Therefore, dedicated engines able to tackle the more challenging mechanical and chemical properties are mandatory for biodiesel in its present form.

Figure 1:
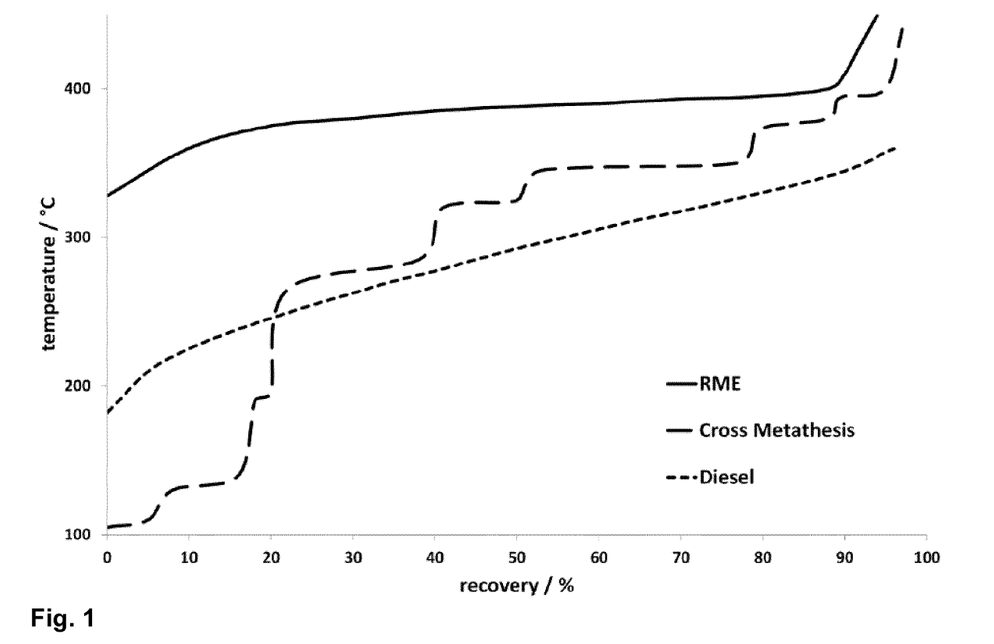
FIG. 1: Schematic boiling point curves of standard petrodiesel (dotted line), pure RME (upper continuous line) and cross-metathesized RME (dashed line).

While solutions have been proposed for some issues associated with FAMEs as biofuels, their unfavourable boiling behaviour remains a major challenge. Petrodiesel has an evenly raising boiling point curve in the range of around 160 to 390° C. (FIG. 1). In contrast, rapeseed methyl esters (RME), which consists mainly of C18 methyl esters, has a disadvantageously narrow boiling range of roughly 330 to 400° C. The initial boiling point of biodiesel is much higher than that of petrodiesel, which affects its ignition behaviour and precludes late-stage injections as are required by modern diesel engines with particulate filters.

The norm EN 590:2013-04 for petrodiesel calls for a smoothly rising boiling point curve to ensure optimal fuel ignition and combustion. At present, vegetable oils need to be converted into mixtures of saturated hydrocarbons by energy-intensive hydroprocessing to comply with this norm and to allow powering standard diesel engines. In search for an alternative, Montenegro and Meier, 2012, have subjected RME to cross-metathesis with 1-hexene and obtained a mixture of olefins, mono- and diesters. In contrast to the smooth petrodiesel curve, however, that of the product mixture has discrete steps and is outside specifications (FIG. 1).

Another method for converting an unsaturated hydrocarbon into a composition of unsaturated hydrocarbons of various chain lengths is isomerizing olefin metathesis. The isomerization and metathesis reaction are carried out simultaneously in the presence of an isomerization catalyst and a metathesis catalyst, both of which are non-selective for specific double-bond positions. The uniquely efficient isomerization catalyst $[Pd(\mu\text{-Br})(tBu_3P)]_2$ constantly converts olefinic substrates into an equilibrium mixture of double-bond isomers. All of these continuously undergo olefin metathesis at an NHC-ruthenium catalyst. By this repetitive, cooperative action, the bimetallic system converts single olefins or olefin mixtures into defined blends with adjustable mean chain lengths.

Ohlmann et al., 2012, have demonstrated that isomerizing metathesis can be used for converting oleic acid ester into a range of unsaturated compounds. Further, the oleic acid ester could be converted into compounds having a smaller average chain length if hexene was added into the reaction. The chain lengths distribution in the product depends on various factors, such as the chain length and ratio of precursors and selection and ratio of the catalysts. However, the method of Ohlmann is not generally applicable for the production of biofuels. At first, it has not been demonstrated that the method is applicable with crude esters derived from vegetable oils. Besides, using large amounts of hexene in an industrial process would be relatively cost intensive. Moreover, hexene is not available from natural sources and is thus would not be an appropriate starting compound for preparing biofuels, which should be derived from natural sources.

Pfister et al., 2015, have suggested that isomerizing metathesis would be a tool for the generation of biodiesel from rapeseed oil in the presence of 1-hexene. However, the process also requires hexene and is thus not applicable for biofuel production for the reasons set out above. Besides, the process conditions and product composition were not disclosed.

Ethylene is an olefin which is available in large amounts and at low costs from natural sources. However, in the methods described above, hexene cannot be simply replaced by ethylene for various reasons. At first, it is difficult to handle gaseous ethylene in such a complex process and for that reason alone liquid hexene cannot simply be replaced by ethylene. More importantly, ethylene is generally known to bind and inhibit standard catalysts for isomerization or metathesis. There, the three different reactions ethenolysis, isomerization and metathesis are generally not compatible.

Baader et al., 2014, have described a method for synthesizing specific organic compounds by isomerizing ethenolysis. However, their method can only be carried out in solvents. Solvents are not applicable for industrial scale production of biofuels because they significantly affect the product and also for cost reasons. In view of these problems, isomerizing ethenolysis for incorporating ethylene into vegetable oils or FAMEs has not been described in the prior art.

In conclusion, there is still a need in the art for efficient methods for producing biofuels and biodiesel from natural sources. Further, there is an ongoing need for improving biofuels such that they meet, or at least come close to, the basic industrial requirements for diesel fuel.

Problem Underlying the Invention

The problem underlying the invention is to provide biofuels and methods for their production which overcome the above mentioned problems.

It is a problem underlying the invention to provide an efficient process for producing biofuels from natural sources, such as vegetable oils. The process shall be relatively efficient and only comprise a low number of process steps. The starting compounds shall be freely available. Furthermore, the process should make use of starting compounds from natural sources, such that the product is a true biofuel.

It is a specific problem underlying the invention to provide a method for producing biofuels, which uses ethylene as a starting compound. Such a method would be more cost efficient than methods with hexene and would enable production of biofuels from exclusively natural precursors.

It is another problem of the invention to provide a biofuel with improved properties, which is applicable as a biodiesel and can be admixed to petrodiesel in large amounts. Thus, the physical properties should be as similar as possible to petrodiesel. It is a special problem of the invention to provide a biofuel which essentially, or fully, meets the standard requirements for petrodiesel as defined in EN 590:2013-04, especially regarding thermal properties or boiling behavior. Specifically, a biodiesel should be provided which has a smoothly rising boiling point curve and optimal fuel ignition and combustion behavior.

Short Description of the Invention

1. A process for producing a biofuel from fatty acid methyl esters (FAMEs) obtained by transesterification of vegetable oils, comprising the steps of
   (a) ethenolysis of the fatty acid methyl esters in the presence of ethylene and an ethenolysis catalyst, and
   (b) isomerizing metathesis in the presence of an isomerization catalyst and a metathesis catalyst.
2. The process according to point 1, wherein the vegetable oil and/or fatty acid methyl esters comprise more than 80 mol-% unsaturated fatty acids, based on the total amount of fatty acids in esterified and free form, wherein the vegetable oil is preferably rapeseed oil, soy bean oil, jatropha oil or tall oil.
3. The process according to at least one of the preceding points, wherein the isomerization catalyst is an organometallic palladium catalyst, preferably bromo(tri-tert-butylphosphine)palladium(I) dimer (IC-1).
4. The process according to at least one of the preceding points, wherein the ethenolysis catalyst and/or the metathesis catalyst are organometallic ruthenium catalysts, preferably N-heterocyclic carbene ruthenium complexes.
5. The process according to at least one of the preceding points, wherein ethenolysis (a) and isomerizing metathesis (b) are carried out simultaneously.
6. The process of point 5, wherein the ethenolysis catalyst is [[1-[2,6-bis(1-methylethyl)phenyl]-3,3,5,5-tetramethyl-2-pyrrolidinylidene]dichloro[[2-(1-methylethoxy-κO)phenyl]methylene-κC]ruthenium(II) (Ru-CAAC),
   wherein preferably the isomerization catalyst is bromo(tri-tert-butylphosphine)palladium(I) dimer (IC-1),
   wherein preferably the metathesis catalyst is selected from [1,3-bis(2,6-diisopropylphenyl)-2-imidazolidinylidene]dichloro[5-(isobutoxycarbonylamido)-2-isopropoxybenzylidene]ruthenium(II) (M73SIPr), [1,3-Bis(2,4,6-trimethylphenyl)-2-imidazolidinylidene]dichloro(2-iodophenylmethylene)ruthenium(II) (M91), and [1,3-Bis(2,6-diisopropylphenyl)-2-imidazolidinylidene]dichloro[(2-isopropoxy)(5-pentafluorobenzoylamino)benzylidene]ruthenium(II) (M72SIMes).
7. The process according to at least one of the preceding points, wherein the ethenolysis catalyst and metathesis catalyst are the same catalyst.
8. The process according to at least one of the preceding points, wherein the process is carried out without solvent.
9. The process according to at least one of the preceding points, wherein the biofuel obtained in step (b) is further processed in post-treatment steps which do not chemically change the chain lengths of the fatty acids, especially in physical treatment steps such as washing, filtration or distillation, or in an adsorptive, antioxidative or sulphur removal treatment.
10. The biofuel obtainable by a process of at least one of points 1 to 9.
11. The biofuel of point 10, wherein the average chain length of the olefins is between 4.5 and 14, and/or the average chain length of the unsaturated monoesters is between 6.5 and 15, and/or the average chain length of the unsaturated diesters is between 7 and 17, wherein all amounts are determined by gas chromatography after hydrogenation.
12. The biofuel of point 10 or 11, wherein the molar amount of compounds comprising more than 22 carbon atoms in the main chain is below 2%, wherein all amounts are determined by gas chromatography after hydrogenation.
13. The biofuel according to at least one of points 10 to 12 having a molecular weight distribution of the olefins and/or of the unsaturated diesters, respectively, which essentially follows an even curve with a single maximum, wherein all amounts are determined by gas chromatography after hydrogenation.
14. The biofuel according to at least one of points 10 to 13, having a boiling curve determined according to EN ISO 3405, which essentially follows a rising curve without peaks or steps at least between 180° C. and 350° C., and/or
    wherein the recovery during boiling at 250° C. is <65%, the recovery at 350° C. is at least 85%, and/or the recovery at 360° C. is at least 95%, respectively determined according to EN 590:2013-04.
15. The biofuel of at least one of points 10 to 14, comprising between 25 to 90% mol-% olefins, 10 to 80% mol-% unsaturated monoesters and 1 to 20 mol-% unsaturated diesters, wherein all amounts are determined by gas chromatography after hydrogenation.
16. The use of ethylene for adjusting and/or optimizing the composition of a biofuel in a method of any of points 1 to 8.

DISCLOSURE OF THE INVENTION

Surprisingly, it was found that the problem underlying the invention is overcome by methods, biofuels and uses according to the claims. Further embodiments of the invention are outlined throughout the description.

Subject of the invention is a process for producing biofuel from fatty acid methyl esters (FAMEs) obtained by transesterification of vegetable oils, comprising the steps of
(a) ethenolysis of the fatty acid methyl esters in the presence of ethylene and an ethenolysis catalyst, and
(b) isomerizing metathesis in the presence of an isomerization catalyst and a metathesis catalyst.

The inventive process is for producing a biofuel. A biofuel is a fuel which is at least in part derived from biomass. Preferably, it is fully derived from biomass. Preferably, the biofuel is a biodiesel. Biodiesel is based on, or comprises a large amount of, fatty acid methyl esters. It is fully miscible with petrodiesel. Preferably, the biodiesel fulfils the requirements laid down in EN 14214:2012, 5.4.3, and thus may be added in an amount of up to 7.0% (v/v) to petrodiesel according to DIN EN 590:2013-12.

The inventive process uses fatty acid methyl esters (FAMEs) as a starting material. Methods for producing FAMEs from vegetable oils by transesterification are well known in the art. In such a process, vegetable oils are processed with methanol, such that the triacylglycerols are converted into FAMEs and glycerol.

Ethenolysis is a chemical process in which internal olefinic compounds are degraded using ethylene as a reagent. The reaction is a specific example of cross-metathesis. As a result, two compounds are obtained containing terminal alkene groups (α-olefinic compounds). Ethenolysis is carried out in the presence of specific metal catalysts with specific binding sites for the volatile low molecular weight ethylene. In the present reaction, the ethylene may react with a monoester, diester or olefin.

Preferably, the ethylene is bioethylene and/or the methanol for producing the FAMEs is biomethanol, i.e. derived from natural sources.

A metathesis is a chemical reaction in which bonds between two reacting compounds are exchanged. Olefin isomerization is a process in which the position of the double bond in an olefinic compound is changed. In isomerizing metathesis, a metathesis reaction and an isomerization reaction proceed simultaneously in the same batch. Since isomerization continuously provides isomers with double bonds at different positions, and metathesis continuously provides products of various chain lengths, an increasingly high number of statistical reaction products are obtained. The basic principle of isomerizing metathesis is shown in scheme 1, which can be found in D. M. Ohlmann, N. Tschauder, J.-P. Stockis, K. Gooßen, M. Dierker, L. J. Gooßen, J. Am. Chem. Soc. 2012, 134, 13716-13729. For example, when a starting compound methyl ester (X=COOMe) is processed with ethylene (Y=H), a blend of olefins, monoesters and diesters will be obtained. As indicated in scheme 1, isomerization catalysts are typically organometallic palladium catalysts and metathesis catalysts are typically organometallic ruthenium catalysts. In an ideal isomerizing metathesis reaction with equal molar amounts of both starting compounds, a bell-shaped homogeneous distribution of the products would be obtained as shown on the right side of scheme 1.

Preferably, the vegetable oil comprises relatively high amounts of unsaturated fatty acids, mostly in the form of esters. In a preferred embodiment, the vegetable oil and/or fatty acid methyl esters comprise more than 80 mol-%, preferably more than 85 mol-% or more than 90 mol-% unsaturated fatty acids, based on the total amount of fatty acids present in esterified and free form. Typically, the double bonds are preserved or essentially preserved in the transesterification process for production of FAMEs. The unsaturated fatty acids may comprise one or more double bonds, for example two, three, four or more double bonds. In principle, the inventive process would also be applicable for vegetable oils comprising lower amounts of unsaturated compounds. However, the resulting product would have less desirable properties, because saturated fatty acids are not convertible in the inventive process and could not be modified accordingly.

In a preferred embodiment, the vegetable oil is rapeseed oil, soy bean oil, jatropha oil or tall oil. These oils have a relatively high content of unsaturated fatty acids.

In a highly preferred embodiment, the vegetable oil is rapeseed oil. Rapeseed oil FAMEs comprise about 65% methyl oleate [18:1], 22% methyl linoleate [18:2], 8% methyl linolenate [18:3], 4% methyl stearate [16:0], and 1% methyl palmitate [18:0]. Thus, the overall content of unsaturated fatty acids is about 95%. Only the remaining 5% stearate and palmitate ester are not convertible in the inventive process and remain in the biofuel product in unmodified form.

In another embodiment, rapeseed methyl ester (RME) is employed, which is a mixture of methyl esters of unsaturated fatty acids with 16 to 22 carbon atoms. Reaction of methanol with refined rapeseed oil yields rapeseed methyl ester as a clear, low viscous, inflammable and water insoluble liquid.

The inventive process requires specific catalysts, which catalyse the three main reactions ethenolysis, isomerization and metathesis. According to the invention, it was found that various catalysts and combinations of catalysts are applicable. Some catalysts are even capable of efficiently mediating ethenolysis and metathesis at the same time. However, it was found that it is crucial to select a combination of catalysts such that an efficient ethenolysis occurs in comparison to the other reactions. Ethenolysis must be able to compete with the other reactions. It was found when ethenolysis proceed too slowly, the desired shift to low molecular weights is insufficient and an undesirable broad molecular weight distribution may be obtained, resulting in undesirable physical properties of the biofuel. Therefore, sufficient introduction of the "building block" ethylene into the target compounds is required during or before isomerization and metathesis. Only then, a strong overall shift to low molecular weights in combination with a relatively low content of undesirable high molecular weight compounds is obtained. This means that either the ethenolysis catalyst must be very efficient, or that the isomerization and/or metathesis catalyst should not be too efficient in order to achieve the necessary balance between ethenolysis and the other reactions. By adjusting this balance with appropriate catalysts and reaction conditions as outlined in the following, a biofuel with excellent physical properties is obtainable.

Preferably, the isomerization reaction is controlled such that no more than 50, preferably no more than 20 isomerization reactions per substrate molecule occur. Preferably, between 2 and 50, more preferably between 4 and 20 isomerization reactions per substrate molecule occur. If the number of isomerization reactions is too high, then the overall molecular weight distribution is too flat and the amount of undesired high molecular weight components is overly high. Preferably, the metathesis reaction is controlled such that at least 1 metathesis reaction, preferably between 5 and 50 metathesis reactions per substrate molecule (unsaturated molecule) of the FAMEs occurs. The number of reactions which has occurred in a given biofuel can be determined from the real biofuel composition by computer modelling the course of the reaction until the theoretical result can be aligned as precisely as possible to the real composition.

In specific embodiments, a specific molecule that is reacted according to the process of the invention more than once at average by both steps a) and b), thus ethenolysis (a) and isomerizing metathesis (b) are carried out repetitively.

The alkene isomerisation catalyst can be a homogeneous or a heterogeneous catalyst.

In a specific embodiment, the isomerization catalyst is an organometallic catalyst, the metal being selected from ruthenium, rhodium, iridium, platinum, palladium and combinations thereof. In yet another specific embodiment, the isomerization catalyst is an organometallic palladium catalyst. Such an organometallic palladium catalyst may contain palladium in different oxidation states, such as Pd(0), Pd(I), Pd(II) or combinations thereof. Preferably, the palladium catalyst contains at least one structural element Pd—P ($R^1R^2R^3$), wherein the $R^1$ to $R^3$ radicals each independently have 2 to 10 carbon atoms, each of which may be aliphatic, alicyclic, aromatic or heterocyclic, with the proviso that at least one of the $R^1$ to $R^3$ radicals contains a beta-hydrogen. The aliphatic radicals may be linear or branched; they may also be in cyclic form; the structural elements mentioned may also be present in combination. Aromatic radicals may also have alkyl substituents. A beta-hydrogen is present when the Pd—P—C—C—H arrangement is present in the palladium catalyst. It was found that such catalysts can be combined in an advantageous manner with catalysts for ethenolysis and metathesis in the inventive process and that such catalyst systems can be adjusted and controlled efficiently.

Preferably, the palladium catalyst does not require a chemical activation by an additional activating substance. The palladium catalyst can be used as such or generated in situ.

The palladium catalyst may be mono- or polynuclear. In one embodiment, the palladium catalyst contains two palladium atoms per molecule. Both palladium atoms may have the same or different oxidation states, which can be selected from Pd(0), Pd(I), Pd(II) or combinations thereof.

In one embodiment, the palladium catalyst contains two palladium atoms per molecule, where the two palladium atoms are joined to one another via a spacer X. Therefore, the palladium catalyst contains the structural element Pd—X—Pd.

The nature of the spacer is not subject to any restriction per se. Suitable spacers X are, for example, halogen, oxygen, O-alkyl, sulphur, sulphur-alkyl, disubstituted nitrogen, carbon monoxide, nitrile, diolefin.

In a preferred embodiment, the palladium catalyst is a compound (I):

in which: X is a spacer selected from halogen, oxygen and O-alkyl, $Y^1$ is a $P(R^1R^2R^3)$ group in which $R^1$, $R^2$ and $R^3$ are each as defined above, $Y^2$ is a $P(R^4R^5R^6)$ group in which $R^4$, $R^5$ and $R^6$ each independently have 2 to 10 carbon atoms, each of which may be aliphatic, alicyclic, aromatic or heterocyclic.

It follows from this definition that the compounds (I) contain at least one beta-hydrogen in the structural element Pd—$Y^1$ (owing to the $R^1$ to $R^3$ radicals present therein). In the structural element Pd—$Y^2$, a beta-hydrogen need not necessarily be present.

In a preferred embodiment, the palladium catalyst is a compound (I-a)

in which X, $Y^1$, and $Y^2$ are defined as outlined for compound (I) above.

Particular preference is given to those compounds (I) or (I-a) in which the spacer is halogen and especially bromine. Very particular preference is given to those in which the spacer X is bromine and the $R^1$, $R^2$ and $R^3$ radicals are each defined as tert-butyl.

In one embodiment, the palladium catalyst is a homogeneous catalyst. In one embodiment, the palladium catalyst is a heterogeneous catalyst. In a specific embodiment, a palladium catalyst of the formula (I) is immobilized via the $Y^1$ and/or $Y^2$ group on a solid substrate or in an ionic liquid.

In a highly preferred embodiment, the palladium catalyst is bromo(tri-tert-butylphosphine)palladium(I) dimer (IC-1, see scheme 2). It was found that this catalyst is more efficient than other palladium based isomerization catalysts. Moreover, it is also compatible with ethylene and other catalysts in the reaction system.

Preferably, the ethenolysis catalyst and/or the metathesis catalyst are an organometallic ruthenium complex. In a preferred embodiment, the ethenolysis catalyst and/or the metathesis catalyst, preferably both, are N-heterocyclic carbene ruthenium complexes. Such catalysts and their applications in olefin metathesis are known in the art. Regarding the structures and reactions, reference is made to Beligny, S. and Blechert, S. (2006), "N-Heterocyclic "Carbene-Ruthenium Complexes in Olefin Metathesis", in N-Heterocyclic Carbenes in Synthesis (ed S. P. Nolan), Wiley-VCH Verlag GmbH & Co. KGaA, Weinheim, Germany. Some catalysts are capable of catalysing ethenolysis and metathesis. It was found that such catalysts can be combined in an advantageous manner with isomerization catalysts in the inventive process and that such catalyst systems can be adjusted and controlled efficiently.

In a preferred embodiment, the ethenolysis catalyst is selected from dichloro(o-isopropoxyphenylmethylene)(tricyclohexylphosphine)ruthenium(II) (HGI, Hoveyda Grubbs I catalyst; scheme 2), [1,3-bis(2,6-diisopropylphenyl)-2-imidazolidinylidene]dichloro[5-(isobutoxycarbonylamido)-2-isopropoxybenzylidene]ruthenium(II) and [[1-[2,6-bis(1-methylethyl)phenyl]-3,3,5,5-tetramethyl-2-pyrrolidinylidene]dichloro[[2-(1-methylethoxy-κO)phenyl]methylene-κC]ruthenium(II) (Ru-CAAC, scheme 2).

In preferred embodiments, the metathesis catalyst is selected from [1,3-bis(2,4,6-trimethylphenyl)-2-imidazolidinylidene]-[2-[[(2-methylphenyl)imino]methyl]-phenolyl]-[3-phenyl-1H-inden-1-ylidene]chloro)ruthenium(II) (Ru-1, scheme 2), [1,3-Bis(2,6-Diisopropylphenyl)-2-imidazolidinylidene]dichloro[5-(Isobutoxycarbonylamido)-2-isopropoxybenzylidene]ruthenium(II) (M73 SIPr, available from Umicore, DE, under the trademark Umicore M73 SIPr, scheme 2), [1,3-Bis(2,4,6-trimethylphenyl)-2-imidazolidinylidene]dichloro(2-iodophenylmethylene)ruthenium(II) (Umicore M91) or [1,3-Bis(2,6-d iisopropylphenyl)-2-imidazolidinylidene]dichloro[(2-isopropoxy)(5-pentafluorobenzoylamino)benzylidene]ruthenium(II) (Umicore M72SIMes). These catalysts may also have some ethenolysis activity.

In a preferred embodiment, the ethenolysis (a) is carried out before isomerizing metathesis (b). Any efficient ethenolysis catalyst, such as HGI or Ru-CAAC, can be used if ethenolysis (a) is carried out before isomerizing metathesis. In this embodiment, the catalyst is preferably removed or inactivated before isomerizing metathesis.

In a highly preferred embodiment, ethenolysis (a) and isomerizing metathesis (b) are carried out simultaneously. In other words, both reactions are carried out in the same batch in the presence of the ethenolysis catalyst, the isomerization catalyst and the metathesis catalyst. The reactions may be carried out simultaneously in part or preferably in full. In such a combined reaction, it is especially preferred that the ethenolysis catalyst is Ru-CAAC. It was found that this catalyst mediates efficient introduction of the "building block" ethylene into the target composition. The catalyst is especially suited for obtaining the desired overall strong shift towards low molecular weight compounds without undesired accumulation of high molecular weight compounds.

Further, it was found that metathesis catalysts M73SIPr, M72SIMes or M91 are efficient if ethenolysis (a) is carried out simultaneously with isomerizing metathesis (b) in the same batch in the presence of Ru-CAAC. These catalysts are highly compatible with each other and also with isomerization catalysts, especially IC-1. Surprisingly, all three reactions proceed in parallel in the presence of these catalysts and ethylene. It was surprising the other catalysts in the batch are not inhibited by ethylene. Moreover, tight control of the product composition and thus physical properties is possible by adjusting the catalyst amounts and conditions.

In a highly preferred embodiment, the ethenolysis catalyst and metathesis catalyst are one and the same catalyst. In this embodiment, the overall reaction only requires two catalysts, the isomerization catalyst and the combined ethenolysis/metathesis catalyst. Thereby, the process is significantly simplified.

In another preferred embodiment, the process is carried out in one single batch, but the ethylene is added later after the isomerizing metathesis has proceeded at least in part or up to equilibrium has been reached. In this embodiment, the isomerization may be inhibited or reduced after addition of ethylene depending on the catalysts used. It was found that also according to this modified process, a biofuel with advantageous properties could be obtained and problems regarding catalyst inhibition by ethylene can be circumvented or reduced.

While addition of reactants or catalysts might be added subsequently over time, it is preferred to carry out the process as a one-pot reaction, wherein all reactants and catalysts are combined and the process is started. The ethylene can be charged as a fixed amount into the reaction container or introduced in a continuous stream.

The reaction temperature can be easily determined by the artisan and is generally from 0° C. to 100° C., more specifically from 20° C. to 80° C., but good results can be obtained at temperatures from 25° C. to 65° C. or from 40° C. to 60° C. as well.

In a preferred embodiment, the molar ratio of ethylene: unsaturated fatty acid methyl esters which participate in the reaction is between 10:1 and 1:10, preferably between 5:1 and 1:5, more preferably between 2:1 and 1:2. The amount of ethylene is selected such that the biofuel has desired properties. The more ethylene is taken up by the target compounds, the lower is the average molecular weight of the biofuel components. Thus, the boiling point curve and other physical properties of the biofuel can not only be controlled by the catalysts used, but also by the amount of ethylene provided, i.e. the availability of ethylene. By increasing the amount of ethylene, the boiling point curve can be shifted to lower temperatures. The use of ethylene is especially advantageous, because the average molecular weight of the compounds can be shifted strongly and in a controlled manner to lower values. A relatively high amount of the resulting biofuel can be evaporated at lower temperatures. Therefore, the biofuel is suitable as a biodiesel. The amount of ethylene used can be lowered when a highly effective ethenolysis catalyst, such as Ru-CAAC, is used in the process.

In a preferred embodiment, the process is carried out without solvent or, more specifically, without additional solvent. Surprisingly, it was found that the overall reaction proceeds when no solvent is added in steps a) and b). This was unexpected, because addition of solvent is required for typical isomerizing ethenolysis reactions described in the prior art. Especially in the single step process, in which ethenolysis and isomerizing metathesis are carried out simultaneously, it was unexpected that catalysts could be identified which mediate the reactions in the absence of solvents. Addition of solvent is often required in the prior art in order to make one or more of the used catalysts available for the reaction due to low solubility, dissolving a greater amount of ethylene in the reaction mixture since it does not dissolve sufficiently in the FAMEs used, or both. Typical solvents used in the prior art are, for example, are hexane, toluene or dichloromethane, which were added as solvent to the reaction mixture or used as solvent for a catalyst solution that was added. Neither of this is necessary according to the invention.

According to the invention, it was found that standard conditions for isomerizing metathesis, for example as described with hexene by Ohlmann et al., 2012, cannot be transferred to the inventive process. Standard ethenolysis catalysts were found not to be compatible with the catalyst system described by Ohlmann et al., 2012. Without being bound to theory, it is assumed that the ethylene inhibits the isomerization catalyst IC-1, possibly by binding of ethylene. Therefore, the inventive process could be a sequential process, in which the ethenolysis (a) is carried before isomerizing metathesis b). Nonetheless, it was necessary to identify solvent free conditions in order to render such a sequential reaction applicable for production of biofuels. As outlined above, the inventors were able to identify catalysts which are compatible and catalyse three different reactions in the same batch. The single step process is supported by special reaction conditions.

In a preferred embodiment, the single step reaction is not carried out at significantly enhanced pressure, preferably below 2 bar or below 1.5 bar. For example, the pressure could be between 0.5 bar and 1.5 bar. Preferably, it is carried out at normal pressure (i.e. without applying under- or overpressure). It was surprising that the reaction was effective at relatively low pressure with specific catalyst systems. Normally, reactions with ethylene are carried out at enhanced pressure in order to support the reaction by shifting the equilibrium to the products. However, it was found that the inventive process can be relatively inefficient under enhanced pressure. Specifically, the performance of the isomerization catalyst IC-1 was found to be low at enhanced pressure. However, when the ethylene is provided at normal pressure, it was found that IC-1 has sufficient activity. In a preferred embodiment, the single step process is carried out such that a constant flow of ethylene is provided to the composition. This can be achieved with special apparatuses, such as a closed glass reactor or steel autoclave. The reaction is preferably carried out under inert conditions in the absence of oxygen.

The amount of catalysts used in the reaction may be between 0.0001 and 1 mol-%, respectively. The amount of ruthenium catalysts for ethenolysis and/or metathesis could be between 0.001 and 0.5 mol-%, and the amount of palladium catalyst for isomerization could be between 0.001 and 0.5 mol-%.

The overall reaction, step (a) or step (b) is terminated when a desired conversion rate has been achieved. The reaction could be terminated by inhibiting or removing the catalysts. The biofuel is separated from the catalysts, for example by mechanical means such as filtration or sieving, or by distillation. In a preferred embodiment, ruthenium catalysts are inhibited with $H_2O_2$ and the aqueous phase is separated from the product. In a preferred embodiment, residual product is obtained from this aqueous phase to increase the yield.

If desired, the biofuel can be processed in post-treatment steps which do not chemically change the chain lengths of the fatty acids. These post-treatment steps could be physical or chemical treatment steps. Preferred are physical treatment steps such as washing, filtration or distillation. Further preferred are adsorptive, antioxidative or sulphur removal treatments. In a specific embodiment, the chemical structure of the olefins and esters is essentially not changed in the post treatment.

Subject of the invention is also the biofuel obtainable by the inventive process. In the following, biofuels are described which are obtainable by the inventive process. By the inventive reaction from FAMEs with ethylene, a specific unique product is obtained.

It was found that the product obtained with ethylene has an advantageous composition of olefins, fatty acid esters and fatty acid diesters, which is not obtainable by known reactions. It would also not be obtainable by metathesis reactions or isomerizing metathesis reactions of comparable FAME compositions with hexene. The reason is that ethylene "imprints" a specific overall molecular weight distribution on the biofuel components, which is never obtainable with hexene due to its higher molecular weight. With hexene, the molecular weight distribution could not be shifted to desired low molecular weights as with ethylene.

If a reaction with hexene would be carried out for a long time, for statistical reasons some low molecular weight compounds would be formed, but at least to the same extent compounds of undesired high molecular weight would be formed, especially those comprising more than 22 carbon atoms (in the main chain, i.e. excluding the methyl ester groups). These high molecular weight compounds have such high boiling points that they cannot be evaporated and adequately combusted under standard conditions in engines. Although a small amount can be tolerated, the quality of the biofuel accumulates significantly when the amount increases to significant levels.

Preferably, the molar amount of compounds comprising more than 22 carbon atoms in the main chain is below 3%, more preferably below 2%, most preferably below 1%. When the molar amount is below 2%, the biofuel can still be combusted adequately and evenly.

The unique molecular weight distribution shifted to lower molecular weights confers advantageous physical properties to the inventive biofuel. Most importantly, the boiling behaviour is very similar to petrodiesel and does not show unfavourable behaviour at high or low temperatures as known from other biofuels. Thus, the inventive biofuel does not cause problems during fuel ignition and combustion and can be admixed to petrodiesel in relatively high amounts. It was even found that a biodiesel can be prepared by the inventive process, which essentially meets the requirements of EN 590:2013-04 for petrodiesel, especially regarding boiling behaviour and the course of boiling point curve.

In principle, a great variety of products is available by the inventive process. The molecular weight distribution of the olefins, monoesters and diesters can be adjusted within broad ranges. For example, the average chain length of the olefins could be between 3.5 and 18, the average chain length of the unsaturated monoesters between 4.5 and 18 and/or the average chain length of the unsaturated diesters between 5.5 and 18. The biofuel could comprise between 5 to 98% mol-% olefins, 10 to 90% mol-% unsaturated monoesters and 0.5 to 25 mol-% unsaturated diesters.

According to this application, the amounts and ratios of components of the biofuel are preferably determined by gas chromatography analysis. Gas chromatography (GC) is the standard industrial method for analysing diesel fuel and biofuels. The composition is hydrogenated before GC analysis. As used herein, all chain lengths or number of carbon atoms for esters relate exclusively to the fatty acid portion, not taking into account the carbon atom of the esterified methanol.

In a preferred embodiment, the average chain length of the olefins is between 4.5 and 14, the average chain length of the unsaturated monoesters is between 6.5 and 15 and/or the average chain length of the unsaturated diesters is between 7 and 17, wherein all amounts are determined by gas chromatography. More preferably, the average chain length of the olefins is between 5.5 and 13, the average chain length of unsaturated monoesters is between 8 and 14, and the average chain length of unsaturated diesters is between 12 and 16. It was found that biofuels comprising such average chain lengths of the main components have especially good thermal properties for biodiesel applications.

In a highly preferred embodiment, the average chain length of the olefins is between 4.5 and 14, especially between 5.5 and 13;
the average chain length of the unsaturated diesters is between 7 and 17, preferably between 12 and 16; and
the molar amount of compounds comprising more than 22 carbon atoms in the main chain is below 2%, wherein all amounts are determined by gas chromatography after hydrogenation. It was found that such a specific combination of average chain lengths in combination with an exclusion of high molecular weight compounds has highly advantageous properties as a biofuel. It can be obtained and adjusted by the inventive method with ethylene as outlined above, especially by balancing ethenolysis with isomerizing metathesis such that a sufficient amount of ethylene is introduced as a building block into the composition.

Figure 2:
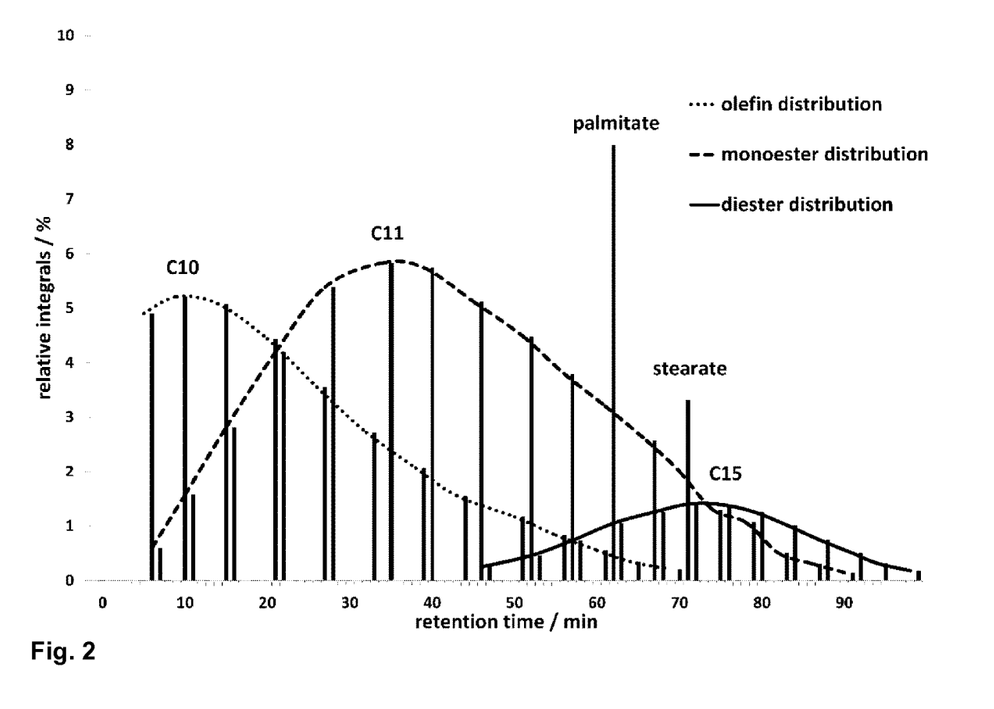
FIG. 2: Mass-corrected gas chromatogram of the hydrogenated product from RME and ethylene produced in a sequential reaction according to example 1.
Figure 3:
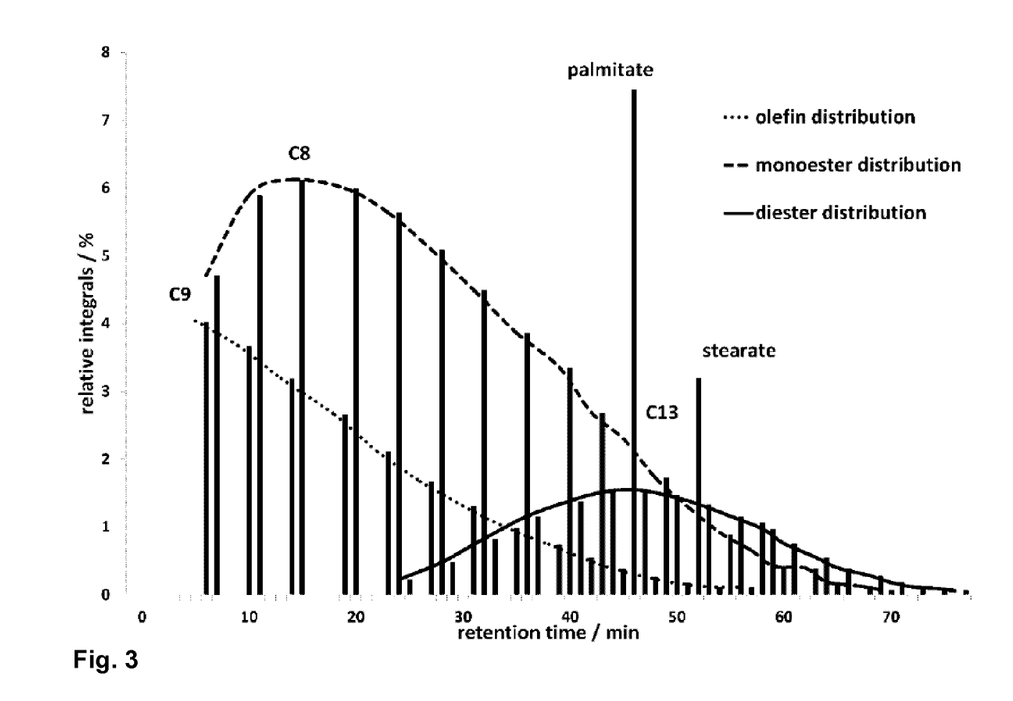
FIG. 3: Mass-corrected gas chromatogram of the hydrogenated product from RME and ethylene produced in a single step reaction according to example 2 (retention times in FIGS. 2 and 3 are not directly comparable due to process variations).

In a preferred embodiment, the biofuel has a molecular weight distribution of the olefins and/or of the unsaturated diesters, respectively, which essentially follows an even curve with a single peak. According to this application, the molecular weight distribution is determined by gas chromatography after hydrogenation. Specifically, the molecular weight distribution of the olefins and/or unsaturated diesters resembles a bell curve, which however normally will be asymmetric. By "even curve" it is meant that the curve for distribution of olefins and/or diesters does not have irregular increases or depressions, and especially not irregular peaks except for the single main peak. However, especially the olefin curve may be "cut-off" at the low molecular weight end. The curves shown for olefins and diesters in FIG. 2 and FIG. 3 are considered to meet this specification. These essentially even curves represent the statistical result of a large number of reactions. The term "essentially" implies that minor errors or variations, for example in the range of up to 2% or up to 5%, cannot be excluded, also due to typical error ranges from determining the amounts by GC. Especially, the essentially even curve should be observed for the 10 most abundant olefins and/or diesters, respectively. It was found that biofuels comprising such homogenous distributions have especially good thermal properties for biodiesel applications.

In FIG. 2 or FIG. 3, it can also be seen that certain monoester peaks fall outside the even curves observed otherwise for the unsaturated monoesters. This is due to an initial content of saturated monoesters in the vegetable oil, which are inert in the inventive process and remain in the product.

Figure 4:
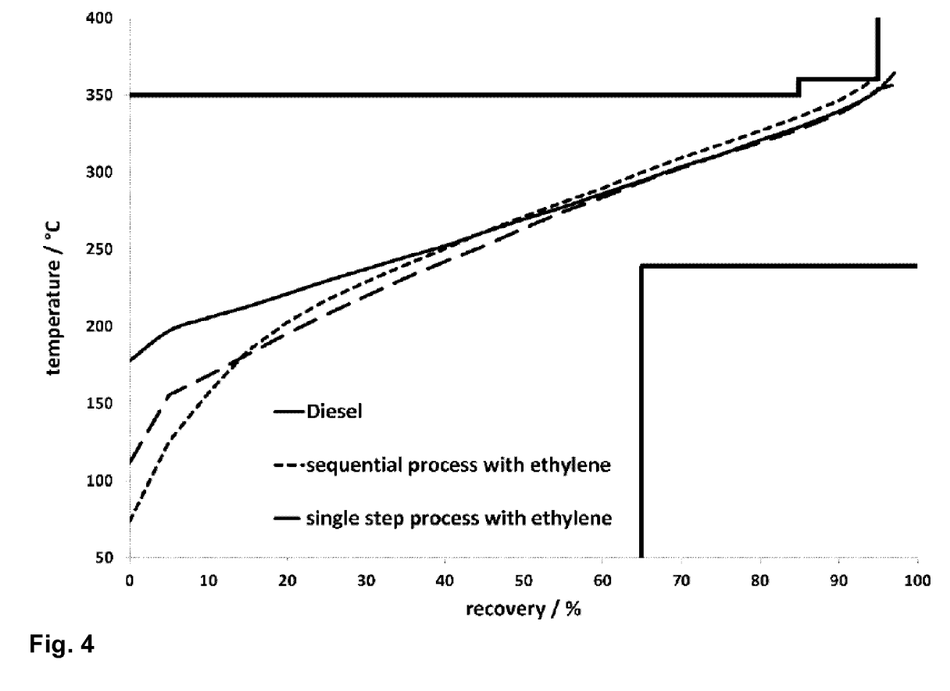
FIG. 4: Boiling curve determined according to EN ISO 3405:2001-04 of the product from RME and ethylene produced in a sequential reaction according to example 1 (dotted line), in a single step reaction according to example 2 (dashed line) and of petrodiesel (continuous line). The areas on the top left and bottom right show the "forbidden" areas for petrodiesel defined in EN 590.

In a preferred embodiment, the biofuel has a boiling curve determined according to EN ISO 3405, which essentially follows a rising curve without peaks or steps. Specifically, an even curve is observed between 180° C. and 300° C., preferably between 100° C. and 350° C. A smoothly rising boiling curve is highly advantageous, because it resembles the boiling behaviour of petrodiesel (FIG. 4). As outlined further above and as shown in FIG. 1, a biofuel with an even boiling curve was not obtainable by cross-metathesis methods described in the prior art. Biofuels with such even boiling point curves have especially good thermal properties for biodiesel applications.

Preferably, the boiling curve starts below 200° C., preferably below 150° C. Preferably, the curve starts above 100° C., more preferably between 100° C. and 150° C.

Preferably, the product passed the ASTM D 6751 (2008) specification for biodiesel because 90% of the composition are distilled below 360° C.

In a preferred embodiment, the recovery at 250° C. is <65% and at 350° C. is at least 85%, determined according to EN 590:2013-04. Thus, the inventive biofuel meets the requirements defined by industrial standards for petrodiesel in this regard.

In a preferred embodiment, the recovery at 360° C. is at least 95%, determined according to EN 590:2013-04. Also in this regard, the inventive biofuel meets the industrial requirements for biodiesel.

In a preferred embodiment, the biofuel comprises between 25 to 90% mol-% olefins, 10 to 80% mol-% unsaturated monoesters and 1 to 20 mol-% unsaturated diesters, wherein all amounts are determined by gas chromatography. Preferably, the total amount of these three main components is at least 90%, more preferably at least 95 wt. % of the biofuel. It was found that biofuels comprising such a content of the main components have especially good thermal properties for biodiesel applications. However, as noted above the molar range of the components can be adjusted over a wide range, depending on the desired product properties. The molar ratios of the components also depend on the vegetable oil, from which the FAMEs are derived, and from the content of unsaturated double bonds in the fatty acids.

According to the invention, it was found that a product as such is applicable as a biofuel or even biodiesel. Thus in a preferred embodiment, the product is not diluted further with hydrocarbons, other esters or organic compounds, especially in order to adjust the thermal properties.

Subject of the invention is also the use of ethylene for adjusting and/or optimizing the composition of a biofuel in the inventive process. Specifically, the use is for adjusting the boiling curve of a biofuel, especially in the lower range between 100 and 200° C. or between 150 and 250° C.

The method, biofuels and uses solve the above mentioned problems. A biofuel is provided with excellent thermal and other properties for use as a biodiesel or admixture to diesel fuels. The composition and thermal properties can be adjusted over a broad desired range. The production process is efficient and convenient and uses ethylene, which is freely available. With bioethylene, a biofuel is obtainable derived completely from natural sources.

Exemplified embodiments of the invention and aspects of the invention are shown in the figures.

EXAMPLES

Catalysts:

In preceding experiments, catalysts were identified which are applicable for a combined ethenolysis and isomerizing metathesis. A large number of experiments and diligent research were necessary to identify catalysts and combinations which are compatible and suitable for simultaneous batch reactions. Known protocols regarding isomerizing metathesis had to be revised considerably in order to overcome the known problems with gaseous ethylene described further above and its inhibitory effect on palladium catalysts. The catalysts identified thereby which are used according to the working examples are summarized in scheme 2 below.

Scheme 2: Preferred catalysts

-continued

M73SIPr

IC-1: Bromo(tri-tert-butylphosphine)palladium(I) dimer; CAS number 185812-86-6; Sigma Aldrich.

Ru-1: [1,3-bis(2,4,6-trimethylphenyl)-2-imidazolidinylidene]-[2-[[(2 methylphenyl)imino]methyl]-phenolyl]-[3-phenyl-1H-inden-1-ylidene](chloro)ruthenium(II); CAS number: 934538-12-2; Umicore M42.

Ru-CAAC: [[1-[2,6-bis(1-methylethyl)phenyl]-3,3,5,5-tetramethyl-2-pyrrolidinylidene]dichloro[[2-(1-methylethoxy-κO)phenyl]methylene-κC]ruthenium(II); CAS number 959712-80-2; prepared according to Lavallo et al., 2005; Marx et al., 2015, and Anderson et al., 2007.

HGI: Dichloro(o-isopropoxyphenylmethylene)(tricyclohexylphosphine) ruthenium(II); CAS number 203714-71-0; Hoveyda Grubbs I catalyst; Sigma Aldrich.

M73SIPr: [1,3-bis(2,6-diisopropylphenyl)-2-imidazolidinylidene]dichloro[5-(isobutoxycarbonylamido)-2-isopropoxybenzylidene]ruthenium(II); CAS number: 1212009-05-6; Umicore M73 SIPr.

Example 1: Sequential Reaction

Step 1: Ethenolysis of RME

Under an atmosphere of argon, a 1 L stirred Parr autoclave was charged with HGI catalyst (Hoveyda Grubbs I; 3.60 g, 600 µmol) and rape seed oil methyl ester (178 g, 200 mL, 600 mmol based on methyl oleate). The vessel was pressurized with 10 bar ethylene and stirred for 16 h at 25° C. The reactor was cooled down to −20° C. and the ethylene pressure was slowly released. After warming up to ambient temperature, the reaction mixture was filtered over silica and distilled under vacuum ($1 \times 10^{-3}$ mbar, up to 250° C.) yielding a mixture of 1-decene and methyl decenoate:methyl oleate:dimethyl octadec-9-enedionate with the ratio 82.7:10.0:5.00 as well as small amounts of additional olefins and saturated components of RME. Due to the reaction being equilibrium, complete conversion could not be achieved. Under the above mentioned solvent-free conditions the excess of ethylene in solution is too small to shift the equilibrium completely to the side of the ethenolysis products.

Step 2: Isomerizing Metathesis

In a glovebox under nitrogen atmosphere, a 100 mL Büchi bmd 075 miniclave drive autoclave was charged with the mixture prepared according to step 1 above (54.0 g, 60.0 mL), IC-1 catalyst (303 mg, 390 µmol) and Ru-1 catalyst (329 mg, 390 µmol). The resulting reaction mixture was stirred for 18 h at 50° C. The reactor was cooled down to ambient temperature and a 30% solution of $H_2O_2$ (27.6 mL, 270 mmol) was slowly added at 0° C. under vigorous stirring (1000 rpm, KPG stirrer). The organic phase was separated, dried over 3 Å molecular sieves and filtered over a short column of celite and $MgSO_4$. Due to RME and therefore the ethenolysis product being mixtures of different compounds, it is only possible to give a yield based on the volume. Starting from 60 mL of the ethenolysis mixture, 50 mL of the isomerizing metathesis blend was isolated (83%). The composition was analyzed by gas chromatography (GC). For facilitating GC, the sample was hydrogenated before analysis. The peaks were assigned by GC-MS and corrected for their mass to generate the histogram of FIG. 2.

Example 2: Single Step Reaction Upscale

In a glovebox under nitrogen atmosphere, a 1 L Parr autoclave was charged with Ru-CAAC catalyst [CAS: 959712-80-2] (243 mg, 0.40 mmol), IC-1 (1.24 g, 1.60 mmol), M73SIPr catalyst (330 mg, 0.40 mmol) and RME (135 mL, 400 mmol based on methyl oleate). The resulting reaction mixture was put under a stream of ethylene at atmosphere pressure and was stirred for 16 h at 60° C. The reactor was cooled down to ambient temperature and a 30% solution of $H_2O_2$ (40.9 mL, 400 mmol) was slowly added at 0° C. under vigorous stirring. The organic phase was separated, dried over $MgSO_4$ and filtered over a short column of celite and $MgSO_4$, yielding 75 mL of a brown oil (55% based on volume). The total yield could be increased to 75% or higher if further product was recovered from the aqueous phase. After distillation in vacuum (1E-3 mbar, >350° C.), the product mixture was obtained as a light yellow liquid (>98 wt-% recovery after distillation). The composition was analyzed by gas chromatography (GC). For facilitating GC, the sample was hydrogenated before analysis. The peaks were assigned by GC-MS and corrected for their mass to generate the histogram of FIG. 3.

Example 3: Single Step Reaction with Optimized Yield

In a glovebox under nitrogen atmosphere, a 30 mL glass reactor was charged with Ru-CAAC catalyst [CAS: 959712-80-2] (30.3 mg, 50.0 µmol), IC-1 (155 mg, 200 µmol), M73SIPr catalyst (41.3 mg, 50.0 µmol) and RME (16.9 mL, 50 mmol based on methyl oleate). The resulting reaction mixture was put under a stream of ethylene at atmosphere pressure and was stirred for 16 h at 60° C. Two of these batches were combined, cooled down to ambient temperature and a 30% solution of $H_2O_2$ (5.11 mL, 50 mmol) was slowly added at 0° C. under vigorous stirring. The organic phase was separated, dried over $MgSO_4$ and filtered over a short column of celite and $MgSO_4$, yielding 25 mL of a brown oil (74% based on volume). After distillation in vacuum (1E-3 mbar, >350° C.), 24 mL of the product mixture was obtained as a light yellow liquid (96% recovery after distillation).

Example 4: Product Properties and Suitability as Biodiesel

The physical and chemical properties of the products of example 1 and 2 and suitability as biodiesel were investigated. Distillation analyses was carried out in an EN ISO 3405:2001-04 apparatus and furnished experimental boiling point curves shown in FIG. 4 (the continuous line is petrodiesel for comparison). Since 90% distilled below 360° C., the product passed the ASTM D 6751 (2008) specification for biodiesel in this regard. It also passed the specifications for petrodiesel fuels detailed in EN 590:2013-04, namely a recovery of <65% at 250° C. and of at least 85% at 350° C. The product of example 1 had about 95% recovery at a maximum of 360° C. The product of example 2 clearly met the requirement of at least 95% at a maximum of 360° C., thus meeting all boiling specifications. In addition, no decomposition was visible during distillation for all products, which is indicative of a low content of undesired components of very high molecular weight and undesired polyunsaturated components. It can be followed that the inventive reaction provides biofuels with excellent physical properties and that the product of the one step reaction is even more advantageous, possible due to a more homogenous composition.

Further analysis using standard methods for fuel testing revealed that the material has a sulphur content of <5 mg/kg, a viscosity of 2.12 mm$^2$/s and a lubricity of 232 μm, all values well within the specifications in EN 590. Moreover, the acid value of 0.360 mg KOH/g is below the threshold for pure biodiesel. Solely the oxidation stability analysis does not yet meet EN 590, but this may certainly be adjusted using standard anti-oxidant additives. The cloud and pour points, which are not explicitly specified, are significantly below 0° C. and thus in a good range for unmodified fuel.

In conclusion, isomerizing metathesis with ethylene allows converting RME into mixtures of olefins and esters that match the boiling behavior of diesel fuel as specified in EN 590. The inventive composition is applicable as a pure biodiesel without the need for dilution with petrodiesel or other hydrocarbons. The inventive technology may turn out to be a decisive breakthrough towards increasing the content of renewables in diesel fuel—ideally up to 100%.

For comparison, an isomerizing metathesis of RME with 1-hexene was put into practice. A high effort was necessary to identify specific catalysts which yield a homogenous product. The 1-hexene/RME product showed a recovery of 93% at 360° C., which misses the value of at least 95% required for petrodiesel. Towards the end of the distillation, the product derived from 1-hexene partially decomposed with smoke formation. This is a common problem for biodiesel, caused by oxidation of sensitive polyunsaturated fatty acid derivatives, and is usually addressed by partial hydrogenation of the product fractions. Further, the hexene product showed a less favourable initial boiling behavior at lower temperatures. Overall, the results demonstrated that the hexene product had different and less advantageous properties, which can be attributed to the higher molecular weight of hexene compared to ethylene and the resulting less favourable molecular weight distribution of the products.

LITERATURE

S. Baader, P. E. Podsiadly, D. J. Cole-Hamilton, L. J. Gooßen, Green Chem. 2014, 16, 4885-4890.
R. E. Montenegro, M. A. R. Meier, Eur. J. Lipid Sci. Technol. 2012, 114, 55-62.
D. M. Ohlmann, N. Tschauder, J.-P. Stockis, K. Gooßen, M. Dierker, L. J. Gooßen, J. Am. Chem. Soc. 2012, 134, 13716-13729.
Kai F. Pfister, Sabrina Baader, 8th Workshop on Fats and Oils as Renewable Feedstock for the Chemical Industry, Mar. 29-31, 2015, Karlsruhe, Germany
V. Lavallo, Y. Canac, C. Prasang, B. Donnadieu, G. Bertrand, Angew. Chem. Int. Ed. 2005, 44, 5705-5709.
V. M. Marx, A. H. Sullivan, M. Melaimi, S. C. Virgil, B. K. Keitz, D. S. Weinberger, G. Bertrand, R. H. Grubbs, Angew. Chem. Int. Ed. 2015, 54, 1919-1923.
D. R. Anderson, V. Lavallo, D. J. O'Leary, G. Bertrand, R. H. Grubbs, Angew. Chem. Int. Ed. 2007, 46, 7262-7265.

The invention claimed is:

1. A process for producing a biofuel from fatty acid methyl esters (FAMEs) obtained by transesterification of vegetable oils, comprising the steps of
(a) ethenolysis of the fatty acid methyl esters in the presence of ethylene and an ethenolysis catalyst, and
(b) isomerizing metathesis in the presence of an isomerization catalyst and a metathesis catalyst, wherein ethenolysis (a) and isomerizing metathesis (b) are carried out simultaneously, wherein between 2 and 50 isomerization reactions and between 5 and 50 metathesis reactions per substrate molecule of the FAMEs occur, and wherein the process is carried out in one single batch and is carried out without an additional solvent, wherein
wherein the isomerization catalyst is an organometallic palladium catalyst containing at least one structural element Pd—P(R$^1$R$^2$R$^3$), wherein the R$^1$ to R$^3$ radicals each independently have 2 to 10 carbon atoms, each of which may be aliphatic, alicyclic, aromatic or heterocyclic, with the proviso that at least one of the R$^1$ to R$^3$ radicals contains a beta-hydrogen
and
wherein the metathesis catalyst is selected from the group consisting of [1,3-bis(2,4,6-trimethylphenyl)-2-imidazolidinylidene]-[2-[[(2-methylphenyl)imino]methyl]-phenolyl]-[3-phenyl-1H-inden-1-ylidene](chloro)ruthenium(II) (Ru-1), [1,3-Bis(2,6-Diisopropylphenyl)-2-imidazolidinylidene]dichloro[5-(Isobutoxycarbonylamido)-2-isopropoxybenzylidene] ruthenium(II) (M73 SIPr), [1,3-Bis(2,4,6-trimethylphenyl)-2-imidazolidinylidene]dichloro(2-iodophenylmethylene)ruthenium(II) (M91), [1,3-Bis(2,6-diisopropylphenyl)-2-imidazolidinylidene]dichloro [(2-isopropoxy)(5-pentafluorobenzoylamino) benzylidene]ruthenium(II) (M721SIMes) and combinations thereof, and
wherein the ethenolysis catalyst is selected from the group consisting of dichloro(o-isopropoxyphenylmethylene) (tricyclohexylphosphine)ruthenium(II) (HGI), [1,3-bis (2,6-diisopropylphenyl)-2-imidazolidinylidene]dichloro[5-(isobutoxycarbonylamido)-2-isopropoxybenzylidene]ruthenium(II), [[1-[2,6-bis(1-methylethyl)phenyl]-3,3,5,5-tetramethyl-2-pyrrolidinylidene]dichloro[[2-(1-methylethoxy-κO) phenyl]methylene-κC]ruthenium(II) (Ru-CAAC) and combinations thereof.

2. The process according to claim 1, wherein the vegetable oil and/or fatty acid methyl esters comprise more than 80 mol-% unsaturated fatty acids, based on the total amount of fatty acids in esterified and free form, wherein the vegetable oil is preferably rapeseed oil, soy bean oil, jatropha oil or tall oil.

3. The process according to claim 1, wherein the isomerization catalyst is a compound (I):

wherein X is a spacer selected from halogen, oxygen and O-alkyl, Y$^1$ is a P(R$^1$R$^2$R$^3$) group, Y$^2$ is a P(R$^4$R$^5$R$^6$) group in which R$^1$, R$^2$, R$^3$, R$^4$, R$^5$ and R$^6$ each independently have 2 to 10 carbon atoms, each of which may be aliphatic, alicyclic, aromatic or heterocyclic, with the proviso that at least one of the $R^1$ to $R^6$ radicals contains a beta-hydrogen.

4. The process according to claim 3, wherein groups $Y^1$ and $Y^2$ are the same.

5. The process according to claim 3, wherein X is bromine and $R^1$, $R^2$, $R^3$, $R^4$, $R^5$ and $R^6$ are each defined as tert-butyl.

6. The process according to claim 1, wherein the ethenolysis catalyst and/or the metathesis catalyst are organometallic ruthenium catalysts.

7. The process according to claim 1, wherein ethenolysis (a) and isomerizing metathesis (b) are carried out repetitively.

8. The process of claim 1, wherein the ethenolysis catalyst is [[1-[2,6-bis(1-methylethyl)phenyl]-3,3,5,5-tetramethyl-2-pyrrolidinylidene]dichloro[[2-(1-methylethoxy-κO)phenyl]methylene-κC]ruthenium(II) (Ru-CAAC), wherein preferably the isomerization catalyst is bromo(tri-tert-butylphosphine)palladium(I) dimer (IC-1), wherein preferably the metathesis catalyst is selected from [1,3-bis(2,6-diisopropylphenyl)-2-imidazolidinylidene]dichloro[5-(isobutoxycarbonylamido)-2-isopropoxybenzylidene]ruthenium(II) (M73SIPr), [1,3-Bis(2,4,6-trimethylphenyl)-2-imidazolidinylidene]dichloro(2-iodophenylmethylene)ruthenium(II) (M91), and [1,3-Bis(2,6-diisopropylphenyl)-2-imidazolidinylidene]dichloro[(2-isopropoxy)(5-pentafluorobenzoylamino)benzylidene]ruthenium(II) (M72SIMes).

9. The process according to claim 1, wherein the ethenolysis catalyst and metathesis catalyst are the same catalyst.

10. The process according to claim 1, wherein the process is carried out at a pressure of 2 bar or less.

11. The process according to claim 1, wherein the process is carried out as a one-pot reaction.

12. The process according to claim 1, wherein the biofuel obtained in step (b) is further processed in post-treatment steps which do not chemically change the chain lengths of the fatty acids, especially in physical treatment steps such as washing, filtration or distillation, or in an adsorptive, antioxidative or sulphur removal treatment.

13. The biofuel obtainable by a process of claim 1.

14. The biofuel of claim 12, wherein the average chain length of the olefins is between 4.5 and 14, and/or the average chain length of the unsaturated monoesters is between 6.5 and 15, and/or the average chain length of the unsaturated diesters is between 7 and 17, wherein all amounts are determined by gas chromatography after hydrogenation.

15. The biofuel of claim 12, wherein the molar amount of compounds comprising more than 22 carbon atoms in the main chain is below 2%, wherein all amounts are determined by gas chromatography after hydrogenation.

16. The biofuel according to claim 12 having a molecular weight distribution of the olefins and/or of the unsaturated diesters, respectively, which essentially follows an even curve with a single maximum, wherein all amounts are determined by gas chromatography after hydrogenation.

17. The biofuel according to claim 12, having a boiling curve determined according to EN ISO 3405, which essentially follows a rising curve without peaks or steps at least between 180° C. and 350° C., and/or
wherein the recovery during boiling at 250° C. is <65%, the recovery at 350° C. is at least 85%, and/or the recovery at 360° C. is at least 95%, respectively determined according to EN 590:2013-04.

18. The biofuel of claim 12, comprising between 25 to 90% mol-% olefins, 10 to 80% mol-% unsaturated monoesters and 1 to 20 mol-% unsaturated diesters, wherein all amounts are determined by gas chromatography after hydrogenation.

19. The use of ethylene for adjusting and/or optimizing the composition of a biofuel in a method of claim 1.

* * * * *